(12) United States Patent
Dicks et al.

(10) Patent No.: US 10,663,463 B2
(45) Date of Patent: May 26, 2020

(54) SYSTEMS AND METHODS FOR THE DETECTION OF BIOMOLECULES

(71) Applicant: Stellenbosch University, Stellenbosch (ZA)

(72) Inventors: Leon Milner Theodore Dicks, Stellenbosch (ZA); Willem Jacobus Perold, Somerset West (ZA); Deon Nevwling, Stellenbosch (ZA); Thomas Stanley Van Den Heever, Somerset West (ZA)

(73) Assignee: Stellenbosch University, Stellenbosch (ZA)

( * ) Notice: Subject to any disclaimer, the term of this patent is extended or adjusted under 35 U.S.C. 154(b) by 424 days.

(21) Appl. No.: 15/124,743

(22) PCT Filed: Nov. 3, 2014

(86) PCT No.: PCT/IB2014/065765
§ 371 (c)(1),
(2) Date: Sep. 9, 2016

(87) PCT Pub. No.: WO2016/071731
PCT Pub. Date: May 12, 2016

(65) Prior Publication Data
US 2017/0023557 A1   Jan. 26, 2017

(51) Int. Cl.
*G01N 33/543* (2006.01)
*G01N 33/551* (2006.01)
(Continued)

(52) U.S. Cl.
CPC ..... *G01N 33/5438* (2013.01); *A61B 5/14735* (2013.01); *A61B 5/6861* (2013.01);
(Continued)

(58) Field of Classification Search
CPC ......... G01N 33/5438; G01N 33/54373; G01N 15/1056; G01N 33/53; G01N 33/551; A61B 5/14735; A61B 5/6861
See application file for complete search history.

(56) References Cited

U.S. PATENT DOCUMENTS

| | | | |
|---|---|---|---|
| 2003/0054355 A1* | 3/2003 | Warthoe | C12Q 1/6825 435/6.12 |
| 2004/0106203 A1* | 6/2004 | Stasiak | G01N 27/3278 422/82.01 |

(Continued)

OTHER PUBLICATIONS

Deon RP. Nevelinga, Thomas S. van den Heeverb, Willie J. Peroldb, Leon M.T. Dicksa; A nanoforce ZnO nanowire-array biosensor for the detection andquantification of immunoglobulins; Sensors and Actuators B 203:102-110 (Jun. 28, 2014).

(Continued)

*Primary Examiner* — Melanie Brown
(74) *Attorney, Agent, or Firm* — Remenick PLLC

(57) ABSTRACT

A system and method for the detection and quantification of biomolecules by measuring a piezoelectric signal is described. The system comprises a plurality of elongate zinc oxide nanowires mounted generally parallel to each another on a semi conductive silicon substrate. The free ends of the nanowires are provided with biomolecules that are capable of associating with complementary biomolecules within a biological or water sample. Following incubation of the system in a sample, the association of molecules of interest with the immobilised biomolecules on the system results in the displacement of the zinc oxide nanowires. The displacement of the nanowires produces a piezoelectric voltage signal that is useful in diagnosing a pathogenic infection or the contamination of a sample.

23 Claims, 8 Drawing Sheets

(51) Int. Cl.
*A61B 5/1473* (2006.01)
*A61B 5/00* (2006.01)
*G01N 15/10* (2006.01)
*G01N 33/553* (2006.01)

(52) U.S. Cl.
CPC ... *G01N 15/1056* (2013.01); *G01N 33/54373* (2013.01); *G01N 33/551* (2013.01); *G01N 33/553* (2013.01); *A61B 2562/0285* (2013.01); *G01N 2015/1062* (2013.01)

(56) References Cited

U.S. PATENT DOCUMENTS

| | | | |
|---|---|---|---|
| 2005/0116263 A1* | 6/2005 | Lu | C12Q 1/6825 257/252 |
| 2007/0210349 A1 | 9/2007 | Lu et al. | |
| 2009/0124025 A1 | 5/2009 | Hamilton et al. | |
| 2010/0176822 A1* | 7/2010 | Offermans | B82Y 15/00 324/663 |
| 2012/0024088 A1* | 2/2012 | Yang | G01G 19/00 73/865 |
| 2012/0184451 A1* | 7/2012 | Singamaneni | B82Y 5/00 506/9 |
| 2013/0017567 A1 | 1/2013 | Lu et al. | |
| 2016/0166184 A1* | 6/2016 | Teng | A61B 5/685 600/347 |

OTHER PUBLICATIONS

Deon RP. Nevelinga;Thesis entitled "Nevelinga, Development of a ZnO nanowire-array biosensor for the detection and quantification of immunoglobulins" (Dec. 13, 2013).

Reyes P I et al: "A ZnO nanostructure-based quartz crystal microbalance device for biochemical sensing", IEEE Sensors Journal 2009 Institute of Electrical and Electronics Engineers Inc. USA, vol. 9, No. 10, 2009, pp. 1302-1307, XP011276017, D0I: 10.1109/JSEN. 2009.2030250 abstract.

Lee D et al: "Enhanced mass sensitivity of ZnO nanorod-grown quartz crystal microbalances", Sensors and Actuators B: Chemical: International Journal Devoted to Research and Development of Physical and Chemical Transducers, Elsevier S.A., CH, vol. 135, No. 2, Jan. 15, 2009 (Jan. 15, 2009), pp. 444-448, XP025949842, ISSN: 0925-4005, D0I: 10.1016/J.SNB.2008.10.026 [retrieved on Nov. 6, 2008] abstract.

Search Report of PCT/IS2014/65765, dated Dec. 5, 2015.
Written Opinion of PCT/IB2014/65765, dated Dec. 5, 2015.

* cited by examiner

SYSTEMS AND METHODS FOR THE DETECTION OF BIOMOLECULES

FIELD OF THE INVENTION

This invention relates to systems and methods for the detection of biomolecules. In particular, it relates to systems and methods for selective detection and quantification of biomolecules associated with a pathogenic infection in humans or the contamination of water.

BACKGROUND TO THE INVENTION

An estimated 250 million people worldwide are infected by pathogenic microorganisms per annum, of which 20 million cases are fatal. Rapid methods of detecting pathogenic infections in humans or the presence of pathogenic agents in water may ensure early diagnosis or prevention of infection, to ultimately reduce the number of fatalities.

A pathogenic infection is caused by a pathogen or infecting agent such as a microorganism, virus, fungus, prion or protozoan and it may cause disease in a host. The immune system of the host launches an immune response when it detects a pathogenic infection, and produces antibodies that recognize a unique part of the foreign target, called an antigen. Antibodies have complementary determining regions that vary so as to be specific for a particular epitope on an antigen, allowing these structures to associate with one another. Antibodies, and their bio recognition capabilities are used extensively as diagnostic tools in a wide variety of analyses. A diagnosis of infection is possible, if it can be determined that a biological sample derived from a subject contains antibodies that selectively associate with a known antigen.

Standard in vitro antibody detection methods such as enzyme-linked immunosorbent assays, magnetic immunoassays, immunoprecipitation, radial immunodiffusion and Western blotting are relatively time consuming techniques and require a skilled person to perform them. Moreover, in a laboratory setting, these methods are more likely to result in diagnostic errors due to human error and the possibility of cross-contamination of samples. Many of the standard methods are qualitative and do not readily allow for the quantification of the amount of antibodies present in a sample.

There thus remains a need for a rapid method of selectively detecting biomolecules, specifically antigens or antibodies linked to pathogenic infection, directly in a subject or within a sample of body fluid obtained from a subject. There also remains a need for the rapid and selective detection of antigens in water samples to determine if the water is contaminated with microorganisms or other pathogenic agents.

SUMMARY OF THE INVENTION

In accordance with a first aspect of the invention, there is provided a system for the detection of biomolecules, comprising a plurality of elongate composite nanostructures having ends mounted on a semi conductive substrate and opposite free ends extending generally parallel to each another, each nanostructure having biomolecules immobilised onto at least a portion of a surface of its free end, wherein, in use, the displacement of the nanostructures owing to the association of a second type of biomolecule with the biomolecules immobilised on the free ends produces a piezoelectric signal.

A further feature provides for the plurality of elongate composite nanostructures to be perpendicularly mounted on the semi conductive substrate.

Further features provide for the semi conductive substrate to be silicon wafers; for a first section of a surface of the silicon wafers to be coated or partially coated with a layer of titanium or titanium oxide; for the titanium/titanium oxide layer to be approximately 20 nm thick; for the titanium/titanium oxide-coated silicon wafers to be coated with a conductive layer, preferably a gold layer that is approximately 40 nm thick; for a zinc oxide (ZnO) seed layer to be provided on the gold layer so as to enable the growth of ZnO nanowires onto the substrate;

for a second section of the surface of the substrate to be coated or partially coated with a conductive layer only, preferably a layer of gold; for the first section of the surface to act as a cathode in use and the second section of the surface to act as an anode in use.

Yet further features provide for the ZnO nanowires to be grown onto the ZnO seed layer so as to extend perpendicularly to the seed layer having a selected length-to-diameter ratio; for a base portion of the elongate ZnO nanowires and the ZnO seed layer to be coated with an insulating layer of material, whilst the free ends of the ZnO nanowires remain uncoated and uninsulated; and for the base portion and the free ends of the ZnO nanowires to be coated with a conductive layer of material.

Still further features provide for the insulating layer of material to be poly(1-vinylpyrrolidone-co-2-dimethylaminoethyl methacrylate); for the conductive layer of material on the free ends of the nanowires to be a gold coating, preferably a 10 nm gold coating; for the gold coating to be provided with molecular scaffolds, preferably self-assembled monolayers (SAMs); for the SAMs to consist of 3-mercaptopropanoic acid; and for the biomolecules to be covalently immobilised to the molecular scaffold.

Yet further features provide for the biomolecules to be antibodies or antigens; for the antibodies or antigens to be proteins; and for primary amino groups of the proteins to covalently bind to the SAMs.

Still further features provide for the system for the detection of biomolecules to be mounted on a board in electronic communication with a measuring system; and for the measuring system to include a receiver and an amplifier circuit including an operational amplifier that is configured to, in use, amplify a voltage obtained from the piezoelectric signal.

A further feature provides for the measuring system to be connected to a converter, configured to convert the amplified voltage into a digital signal, an operating system with a program that issues machine-readable instructions to record, analyse and process the digital signal, a user interface for providing access to processed signal data on an electronic device.

Yet a further feature provides for a part of the system for the detection of biomolecules to be contained in a capsule, preferably a gelatine capsule so as to allow it to be swallowed by a patient.

Still a further feature provides for the system for detecting biomolecules to be used to detect viral and microbial infection in biological samples obtained from a patient, preferably body fluids.

Yet a further feature provides for the system to be used to detect biomolecules in water samples.

In accordance with a second aspect of the invention there is provided a method of detecting biomolecules, the method comprising the steps of:

immersing a system for detecting biomolecules, as defined above, within a biological sample;

measuring a change in voltage by means of a measuring system, as defined above, connected to the system for detecting biomolecules; and determining an amount of biomolecules that are associated with biomolecules immobilised on the system based on a change in voltage measured.

Further features of the second aspect of the invention provide for the method of detecting biomolecules to include the steps of amplifying the change in voltage measured by the measuring system to produce an amplified voltage signal; converting the amplified voltage signal to a digital signal; recording, analysing and processing the digital signal; displaying an amount of biomolecules detected; and assigning a level of pathogenic infection in a subject or contamination in a sample.

Yet further features of the second aspect of the invention provide for the method of detecting biomolecules to be carried out in vivo as a method of diagnosing disease in a subject, preferably infectious disease caused by a pathogenic infection; and for the method to include a step of swallowing a part of the system for detecting biomolecules contained in a capsule or implanting a part of the system for detecting biomolecules in the subject.

Further features of the second aspect of the invention provide for the method of detecting biomolecules to be carried out in vitro as a method of diagnosing disease in a subject, preferably infectious disease caused by a pathogenic infection; and for the method to include the steps of collecting a biological sample from a human, preferably body fluid; and immersing the system for detecting biomolecules or part of the system in the biological sample.

Further features of the second aspect of the invention provide for the method of detecting biomolecules to be carried out in vitro as a method of detecting contamination in a water sample; and for the method to include the steps of collecting a water sample and immersing the system for detecting biomolecules or part of the system in the water sample.

A further feature of the second aspect of the invention provide for the method of detecting biomolecules to include the step of providing an incubation time so as to allow biomolecules in the biological or water sample to associate with the biomolecules immobilised on the system.

The above and other features of the invention will be more fully understood from the following description and the accompanying drawings.

DETAILED DESCRIPTION WITH REFERENCE TO THE DRAWINGS

Figure 1:
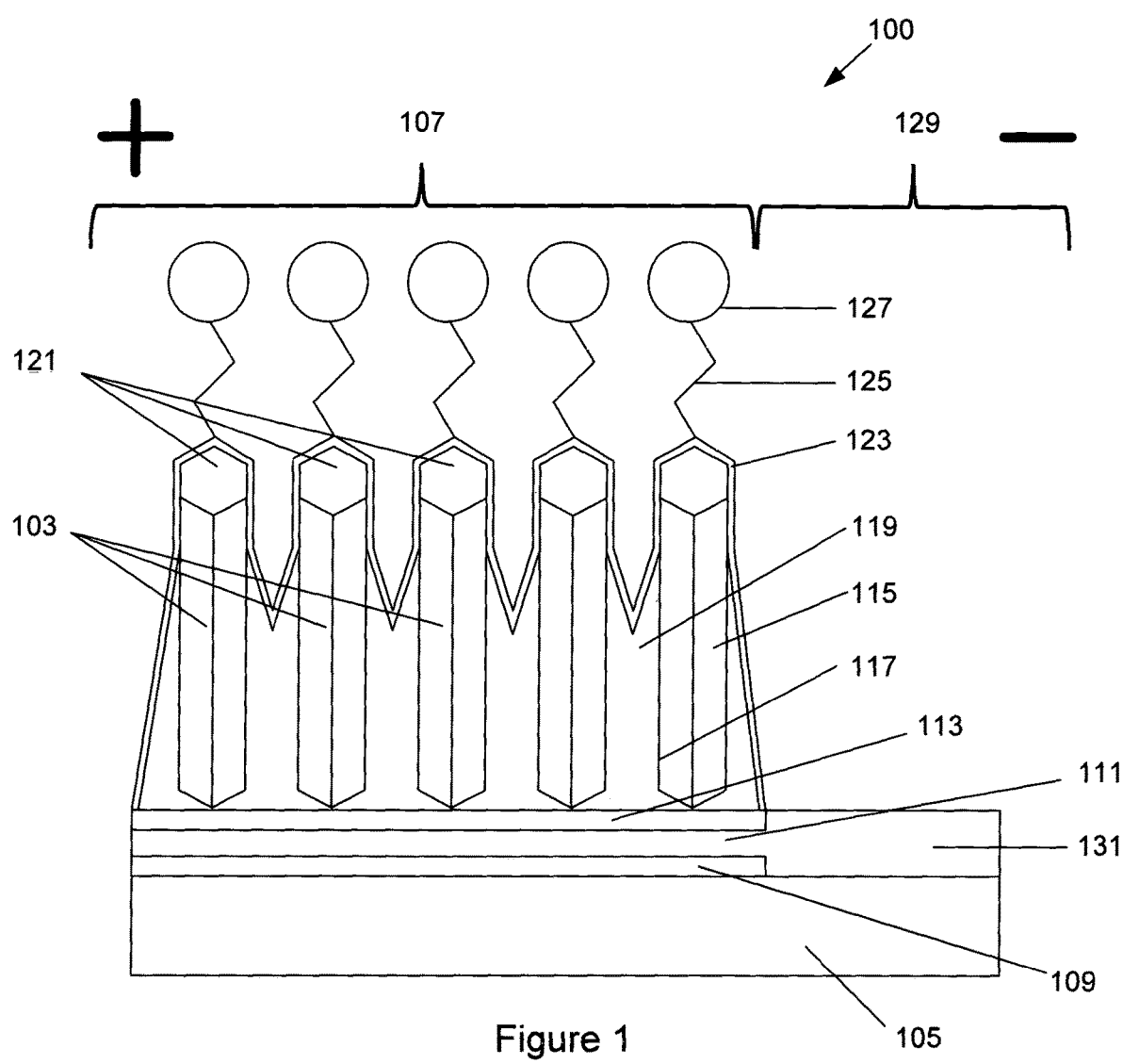
FIG. 1 is a schematic diagram of an embodiment of the system for the detection of biomolecules according to the invention.

FIG. 1 is a schematic diagram of an embodiment of a system for the detection of biomolecules (100). The system (100) includes an array of composite nanostructures (103) mounted on a semi conductive substrate (105) made of silicon wafers. The substrate is partially coated on a first section (107) of the surface thereof with a 20 nm layer of titanium or titanium oxide (109). Other possible coatings include tin or tin oxide. The titanium/titanium oxide layer (109) is further coated with a 40 nm layer of gold (111). A ZnO seed layer (113) is provided on top of the gold layer (111). In this embodiment, the nanostructures (103) are elongated ZnO nanowires (115) that are grown onto the ZnO seed layer (113) in a direction perpendicular to the surface of the substrate by means of a hydrothermal growth method. A base portion (117) of the elongate ZnO nanowires (115) and the ZnO seed layer (113) are coated with an insulating layer of poly(1-vinylpyrrolidone-co-2-dimethylaminoethyl methacrylate) (PMMA) (119). The free ends (121) of the ZnO nanowires (115) are not coated with PMMA and remain uninsulated. The entire first section (107) of the surface of the substrate, including the free ends (121) of the ZnO nanowires (115), is completely coated with a conductive layer of gold (123). Self-assembled monolayers (SAMs) (125), in this embodiment 3-mercaptopropanoic acid molecules, self-assemble onto the gold layer (123). The SAMs (125) act as molecular scaffolds to which biomolecules (127), such as antigens or antibodies are covalently bound. In the case that the biomolecules are proteins, the primary amino groups of the protein react with the 3-mercaptopropanoic acid SAMs to form covalent amide bonds. A second section (129) of the surface of the silicon substrate is coated with a layer of gold (131) only, which, in use, acts as an anode, whilst the first section of the surface of the substrate that supports the ZnO nanowires is a semiconductor, which, in use, acts as a cathode.

The metal-semiconductor junction, in this embodiment the free ends (121) of the ZnO nanowires (115) that are only coated with the gold layer (123), creates a Schottky barrier for the production of a piezoelectric signal, observed as an increase in voltage. In use, the array of nanostructures produces a piezoelectric signal when the nanostructures are subject to tensile pressure that causes them to bend. If a large number of complementary biomolecules, in this embodiment the complementary antibodies to the antigens bound to the SAMs, associate with the antigens owing to bio recognition, it induces the ZnO nanowire to bend and a piezoelectric signal results.

Changes in voltage from the piezoelectric signal is measured by a measuring system in electronic communication with or connected to a circuit board onto which the system for the detection of biomolecules is mounted. The measuring system includes a receiver and an amplifier circuit with an operational amplifier connected across a resistor that is configured to, in use, amplify the voltage obtained from the piezoelectric signal.

Figure 2:
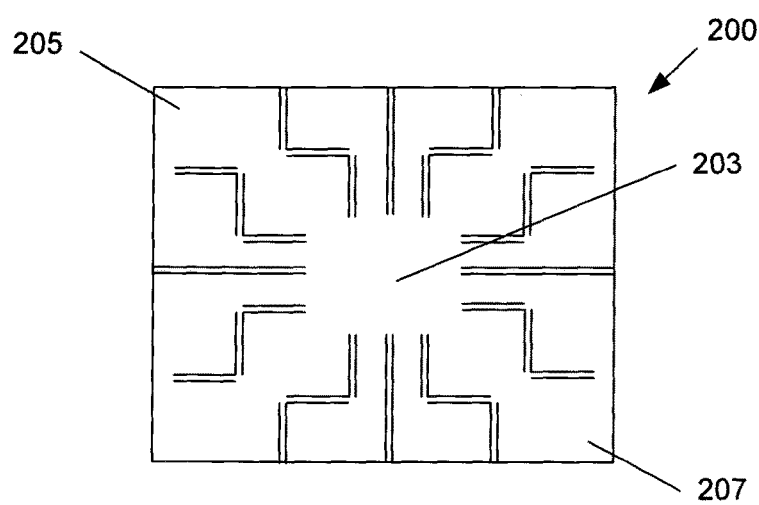
FIG. 2 is a schematic diagram which illustrates an exemplary board onto which the system of FIG. 1 may be mounted.

FIG. 2 is a schematic diagram which illustrates an exemplary circuit board (200) onto which the system of FIG. 1 may be mounted. The system of FIG. 1 (not shown) is mounted in the centre (203) of the board of FIG. 2. Two opposite corners (205 and 207) of the board are connected to a conducting line (not shown) with silver paste (not shown). The conducting line is connected to a receiver (not shown). The anode (not shown) of the system for the detection of biomolecules is connected to ground and the cathode (not shown) of the system is connected to the positive terminal (not shown) of the receiver. In an alternative embodiment of the invention for use in the detection of biomolecules in vivo, the receiver is not physically connected to the system, instead an external antenna system is coupled to the amplifier.

Figure 3:
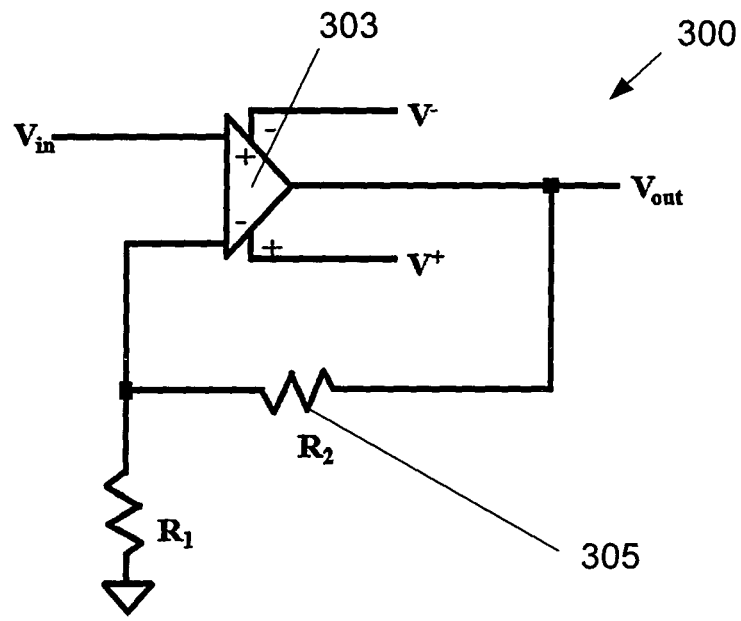
FIG. 3 is a schematic diagram which illustrates an exemplary amplifier circuit.

FIG. 3 is a schematic diagram which illustrates an exemplary amplifier circuit (300). Changes in voltage produced by the piezoelectric signal ($V_{in}$) is measured using an operational amplifier (303) connected across a resistor, $R_2$ (305). In the current embodiment, an operational amplifier with a gain of 100V/V is used. The amplified voltage ($V_{out}$) in analogue format is converted to a digital signal using a converter (not shown), such as a LabJack U6 converter. The digital signal is recorded, analysed and processed on an operating system (not shown) with a software program that issues machine-readable instructions. In this embodiment DAQFactory software from Azeotech Inc., OR, USA is used to analyse the digital signal. The program also has a user interface for providing access to processed signal data on an electronic device (not shown).

The system for the detection of biomolecules is a miniature system. The silicon wafers of the current embodiment are approximately 1 cm×1 cm in size. It will be appreciated by someone skilled in the art, that the size of the system may be reduced even further. The self-powered miniature system for the detection of biomolecules or part of the system may be contained in a capsule, preferably in a gelatine capsule, so as to allow it to be swallowed by a patient. After the gelatine capsule dissolves in vivo, i.e. in the stomach, the system for the detection of biomolecules is immersed in biological stomach fluid allowing it to detect the presence of biomolecules that are complementary to, and associate with, the biomolecules immobilised on the system to thereby produce a measurable signal.

In an alternative embodiment of the system for the detection of biomolecules, the system is not contained in a capsule, but rather forms part of a diagnostic kit that is used to detect viral and microbial infection in biological samples, preferably body fluids such as sputum, blood, sweat, semen, vaginal secretions or tissue, or as a kit for detecting biomolecules in water samples. In such an embodiment of the invention, the system is simply immersed in a sample of the fluid in order to selectively detect biomolecules complementary to those immobilised on the system.

Figure 4:
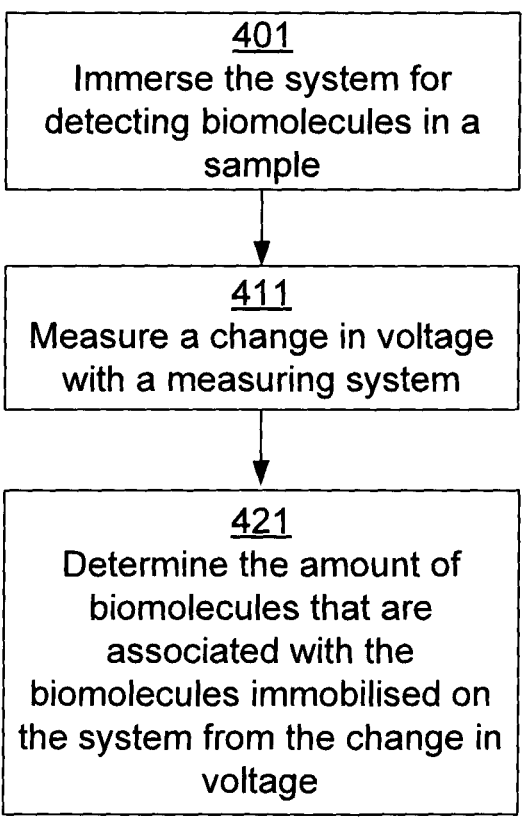
FIG. 4 is a flow diagram which illustrates exemplary methods of detecting biomolecules.

FIG. 4 is a flow diagram which illustrates exemplary methods of detecting biomolecules. At a first step (401) the system for the detection of biomolecules is immersed in a biological sample. A change in voltage is measured by means of a measuring system connected to the system for the detection of biomolecules at a second step (411). At a final step (421), the amount of biomolecules that are associated with biomolecules immobilised on the system is determined based on a change in voltage measured.

Figure 5:
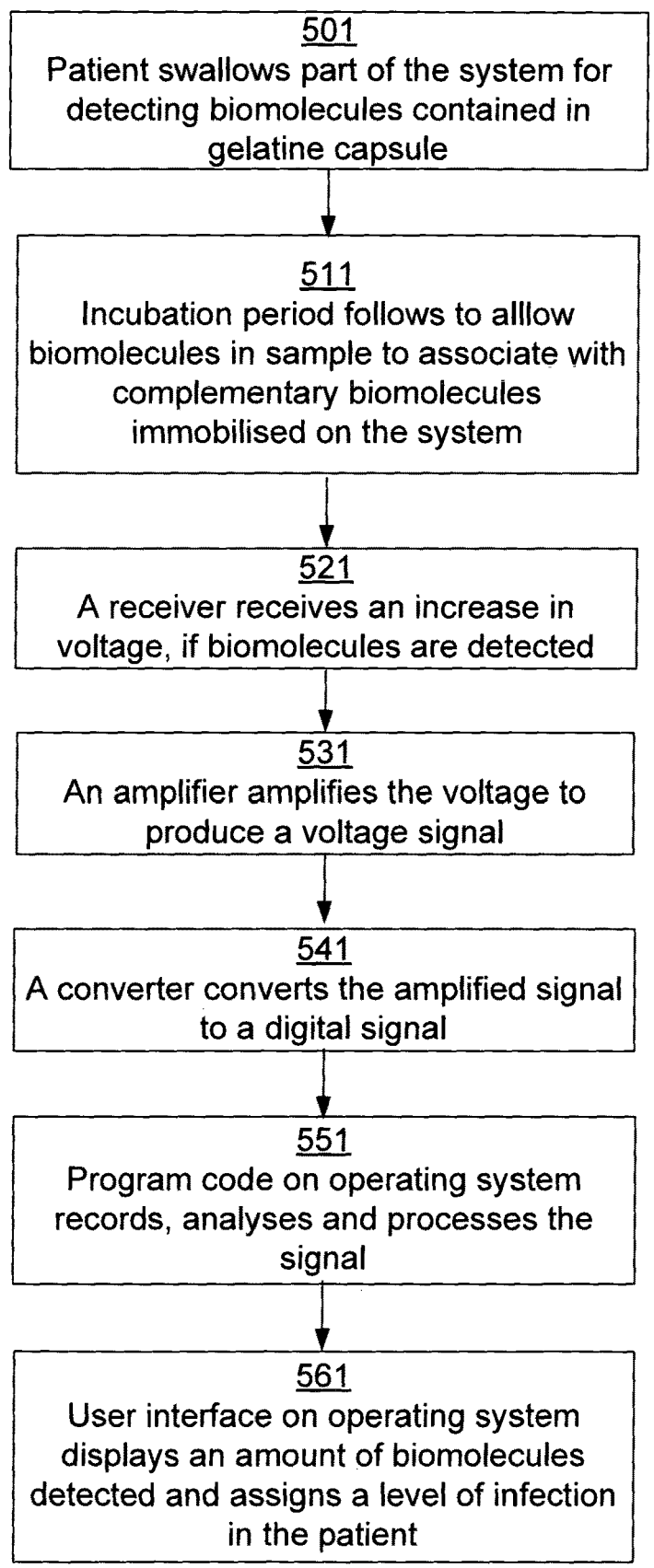
FIG. 5 is a flow diagram which illustrates further method steps for obtaining a diagnosis of an infection using the method of FIG. 4.

FIG. 5 is a flow diagram which illustrates further method steps for obtaining a diagnosis of an infection in a human subject or patient using the method of FIG. 4. In this embodiment of the method, the method of detecting biomolecules is carried out in vivo as a method of diagnosing disease, preferably infectious disease caused by a pathogenic infection. At a first step (501) a patient swallows a part of the system for the detection of biomolecules contained in a gelatine capsule. At a second step (511), an incubation period follows to allow the gelatine to dissolve so as to immerse the system for the detection of biomolecules in the stomach fluid and to allow the biomolecules in the fluid to associate with the complementary biomolecules immobilised on the system. Whilst the system is incubated, a receiver in electronic communication with or connected to a circuit board onto which the system is mounted receives a voltage. If a sufficient amount of biomolecules have associated with the system to produce a piezoelectric effect, the receiver receives an increase in voltage at a further step (521). An operational amplifier in an amplifying circuit amplifies the increase in voltage or voltage input to produce a stronger voltage signal or voltage output at step (531). At a next step (541), a converter connected within the measuring system converts the amplified signal, which is in an analogue format to a digital signal. The digital signal is recorded, analysed and processed into an understandable format by a suitable program resident on an operating system at step (551). Communication between the capsule and the system hosting the operating system may be by means of low-powered wireless communication. At a final step (561) a user interface of the program displays the amount of biomolecules that were detected based on the voltage derived from a piezoelectric effect and may assign a level of pathogenic infection in the patient, depending on whether biomolecules were detected, and a calculation of how many molecules were detected based on the voltage output.

In another embodiment of the method for detecting biomolecules in which the system is used in vitro rather than in vivo, the method includes the steps of collecting a biological sample from a human, preferably a body fluid such as sputum, blood, sweat, semen, vaginal secretions or tissue sample or a contaminated water sample and immersing the system for detecting biomolecules or part of the system in the biological or water sample. The detection of the biomolecules will occur by means of a piezoelectric signal, in a similar manner as described above.

ZnO nanowires are biocompatible, chemically stable and non-toxic, which renders them excellent candidates as transducers for devices or systems that detects biomolecules in vivo. At ambient temperature and pressure, ZnO crystallizes in a wurtzite structure with a hexagonal lattice. The tetrahedral coordination of ZnO molecules along the hexagonal axis leads to the formation of piezoelectric energy and the elongate nanowire structure acts as a semiconductor with high bandgap energy (3.37 eV at room temperature).

The small diameter of the ZnO nanowires renders them excellent nanotransducers. The piezoelectric potential at the surface of nanowires is directly proportional to the lateral displacement of the nanowires due to bending and inversely proportional to the length-to-diameter ratio of the nanowires. Voltage output increases with an increase in nanowire length within the range of approximately 600-4000 nm, but decreases if the length exceeds approximately 4000 nm. The voltage output of a piezoelectric nanowire increases with a decrease in nanowire diameter. This is because a decrease in the nanowire diameter results in an increase in the aspect ratio and deflection, leading to an increased voltage signal. The best piezoelectric signals are obtained with the ZnO nanowire crystals perpendicularly aligned to the substrate surface, i.e. aligned along the crystallographic c axis.

Further ZnO nanostructures with high sensitivity owing to a large surface area for maximal loading capacity of biomolecules and suitably small diameters include nanobelts, nanosprings, nanorings, nanohelices, nanobows, nanowires, nanotubes, nanocages, nanoshells, nanospheres, nanofibres, nano-tetrapods, nanonails and nanobridges.

It will be appreciated by those skilled in the art that numerous different techniques may be used to synthesise ZnO nanostructures, for example, growth in vapour, liquid and solid phases, the deposit of ZnO with laser technology, electrochemical interactions, transport of Zn, ZnO and zinc acetylacetonate in vapour, the use of diethylzinc and $O_2/N_2O$ as precursors and hydrothermal growth. The hydrothermal growth method is less expensive, is performed at lower temperatures in comparison to the vapour phase techniques, allows for a greater choice of inorganic and organic substrates and production is easier to scale up.

Growth of ZnO crystals directly onto silicon is difficult, due to the presence of lattice and thermal mismatches between the ZnO crystal nuclei and silicon. Surface atoms on a silicon (Si) (100) surface are aligned to form a square pattern, opposed to a hexagonal pattern observed on a Si (111) substrate. Due to this, Si (111), and not Si (100), forms a better combination with the ZnO framework. However, ZnO nanowires forming on Si (111) have larger diameters compared to nanowires that formed on Si (100) and they are more crystalline. Superior alignment of the ZnO nanowires is achieved by introducing a ZnO seed layer. The thinner the seed layer, the thinner the nanowires. Seed layers may be deposited by chemical vapour deposition, reactive evaporation, pulsed laser ablation, sputtering, spray pyrolysis, hydrothermal reactions or sol-gel spin coating. The mean diameter and length of ZnO nanowires are regulated by precursors. A precursor such as hexamethylenetetramine (HMTA) decomposes to formaldehyde, ammonia and hydroxide anions. This is important in the formation of ZnO axial growth and exposes the nanostructures to the (0001) plane.

It will be appreciated by those skilled in the art that various different methods may be used to prepare the system for the detection of biomolecules without departing from the scope of the invention. It will be understood, however, that the methods used in providing the substrate with the various layers of different materials will subsequently effect the growth of the ZnO nanowires on the substrate. For instance, the effect of the gold layer beneath the ZnO seed layer; the thickness of the seed layer; and, the crystal orientation of the seed layer on the morphology and alignment of ZnO nanowires synthesised by the hydrothermal method have been assessed by the applicant. ZnO seed layers deposited by the sol-gel spin coating technique or by the RF cylindrical magnetron sputtering technique were characterized by atomic force microscopy (AFM) and ellipsometry. ZnO nanowires hydrothermally synthesised were characterized by scanning electron microscopy (SEM), energy-dispersive x-ray spectroscopy (EDS), transmission electron microscopy (TEM) and X-ray diffraction (XRD).

The experimental details and a summary of the results of the tests and assessments of ZnO nanowire growth follow herein below.

EXPERIMENTAL DETAILS

I Preparation of Silicon Wafers

Silicon (100) wafers were cut into 1×1 cm sizes and sonicated for 10 min in acetone, followed by 10 min in absolute ethanol and 10 min in distilled water. The wafers were dried under nitrogen gas and placed on a hot metal plate (110° C., 5 min) and then immersed in 40% (v/v) hydrofluoric acid for 30 seconds to enhance bonding between the silicon and gold atoms. The wafers were then rinsed in distilled water, dried under nitrogen gas and heated on a hot plate as before, and placed in an Edwards S150B sputter coater (Edwards, West Sussex, UK). A 40 nm gold film layer was sputtered onto the silicon wafers at 1.5 kV and 20 mA, under $2 \times 10^{-1}$ mbar pressure and in the presence of argon.

II Deposition of the ZnO Seed Layers

The gold-plated silicon wafers were cleaned by rapid immersion in absolute ethanol to remove surface impurities, dried under nitrogen gas and placed on a hot plate at 110° C. for 5 min. ZnO seed layers were deposited by either the sol-gel spin coating or the RF cylindrical magnetron sputtering techniques. The seed layer solution for the sol-gel spin coating technique was prepared by dissolving 0.75 M zinc acetate dehydrate ($C_4H_{18}O_8Zn$) in a combination of 2-methoxyethanol ($C_3H_8O_2$) and monoethanolamine ($C_2H_7NO$). The molar ratio of monoethanolamine to zinc acetate was 1:1. The seed layer solution was stirred for 1 h at 60° C. and 25 µl was placed onto the gold-plated Si wafers and spun in a Laurell WS-400-6NPP spin coater (Laurell Technologies, Pennsylvania, USA) at 3000 rpm for 30 sec.

After spin-coating, the solvent and residual organic components were removed by drying the wafers at 200° C. for 5 min on a hot plate. The spin coating procedure was repeated up to six times. Upon completion of spin coating the seed layers were annealed in air in a furnace at 700° C. for 10 min.

With the RF cylindrical magnetron sputtering technique, ZnO was deposited under $2\times10^{-2}$ mbar pressure in the presence of 60% oxygen and at 100 W. The deposition time varied from 1 to 6 min.

III Effect of Gold Layer Thickness on the Growth of ZnO Nanowires

To determine the effect gold film layer thickness has on the growth of ZnO nanowires synthesized using hydrothermal growth, gold film layers of different thicknesses were used. Silicon wafers were prepared as before (section I). However, after etching with hydrofluoric acid, the wafers were sputtered with gold using an Edwards S150B sputter coater, as described before (section I), to yield layers of 20, 40 and 60 nm thick. The ZnO seed layers were deposited for 3 min using the RF cylindrical magnetron sputtering technique under $2\times10^{-2}$ mbar pressure in the presence of 60% oxygen and at 100 W.

IV Effect of Gold Crystal Orientation on the Growth of ZnO Nanowires

To determine the effect gold crystal orientation has on ZnO nanowire growth, single and polycrystalline gold film layers were used. Silicon wafers were prepared, as described before (Section I), and sputtered with a single crystalline gold film layer (40 nm) by using an Edwards S150B sputter coater, as described before (Section I). Hydrothermal evaporation was used to deposit polycrystalline gold film layers, the chamber was evacuated to $2\times10^{-5}$ mbar and the thickness of the gold film layer (40 nm) controlled using a QCM sensor (Sigma Instruments, Colorado, USA). ZnO seed layers were deposited for 3 min, using the RF cylindrical magnetron sputtering technique under $2\times10^{-2}$ mbar pressure and in the presence of 60% oxygen and at 100 W.

V Synthesis of ZnO Nanowires

ZnO nanowires were synthesized using hydrothermal growth. Gold-plated silicon wafers, coated with a ZnO seed layer, were placed in a solution of 0.01 M zinc nitrate hexahydrate [$Zn(NO_3)_2.6H_2O$] and 0.01 M hexamethylenetetramine ($C_6H_{12}N_4$) in distilled $H_2O$ for 7 h in an oven at 90° C. After nanowire growth, residual salts and amino complexes were removed by washing with distilled water, dried under nitrogen gas and placed on a hotplate at 110° C. for 5 min. The wafers were then heated to 350° C. and kept at this temperature for 30 min.

VI Characterisation of ZnO Nanowires

An atomic force microscope (AFM) Easyscan 2 (Nanosurf Inc., California, USA) was used to characterize the surface topology and to determine the surface roughness of the ZnO seed layers deposited by the sol-gel spin coating and RF cylindrical magnetron sputtering techniques. A Woollam J.A. M-2000 variable angle spectroscopic ellipsometer with a rotating analyser, VASE (J.A. Woollam Co. In., Nebraska, USA), was used to determine the surface thickness of the ZnO seed layer films that were deposited.

The surface morphology, diameter and density of the synthesized ZnO nanowires were evaluated using a FEI Nova NanoSEM 230, equipped with a TLD detector (FEI, Oregon, USA). The purity and elemental composition of the ZnO nanowires were analysed by energy-dispersive x-ray spectroscopy (EDS), using a FEI Nova NanoSEM 230, equipped with an X/Max Oxford energy-dispersive x-ray (EDX) detector (Oxford Instruments, Oxfordshire, UK) with a detector area of 20 $mm^2$. Energy dispersive spectroscopy (EDS) spectrums were analysed using INCA software (Inca Software, Berkshire, UK).

Transmission electron microscopy (TEM) micrographs were recorded with a FEI Tecnai G2 F20 TEM (FEI, Oregon, USA), of which the LaB6 filament was set at an accelerating voltage of 200 kV. Specific area electron diffraction (SAED) patterns were selected and collected on a Philips Tecnai TF20 TEM (FEI, Oregon, USA), equipped with a field emission gun and operated at an accelerating voltage of 200 kV. High resolution transmission electron microscopy (HR-TEM) images were used to study the crystal structure of the ZnO nanowires and indicate whether the axial growth is along the [0001] direction. The mean length and diameter of the ZnO nanowires were also determined using TEM microscopy. ZnO nanowires were scratched from the substrate surface, dissolved in absolute ethanol and ultrasonicated for 10 seconds. A drop of the liquid was placed on a Cu grid that was covered with a carbon film. The samples were air dried before analysis.

The ZnO nanowires, Au film layer crystal structures and phase compositions were determined by x-ray diffraction (XRD), using a Bruker AXS D8 Advance X-ray diffractometer operated in locked coupled mode (Bruker AXS, Frankfurt, Germany). The instrument was equipped with a Vantec-1 position sensitive detector optimized for Cu-Kα radiation with $\lambda=1.5406$ Å. The X-ray tube was set at 40 mA and 40 kV and the measurements were recorded at a scanning rate of 0.5 sec/step with a step size of 0.014° in a 2θ range extending from 31.28° to 149.3°.

SUMMARY OF THE RESULTS

I Seed Layer Deposition

In both seed layer deposition techniques an increase in ZnO deposition resulted in an increase in the mean ZnO seed grain diameter. With an increase in ZnO deposition, using the sol-gel spin coating technique, the surface roughness increased. However, when RF cylindrical magnetron sputtering was used, a decrease in surface roughness was observed.

With an increase in ZnO seed layer thickness by either deposition technique results in an increase in the mean diameter of the synthesized ZnO nanowires. The average length of ZnO nanowires synthesized for a growth period of 7 hours were between 1.6 and 1.7 μm for ZnO nanowires synthesized on both of the ZnO seed layers produced by either deposition technique.

An increase in the ZnO seed layer thickness deposited by the RF cylindrical magnetron sputtering technique improved the c-axis orientation of the synthesized ZnO nanowires. It is believed that increasing the seed layer surface roughness and improved the c-axis orientation of the ZnO nanowires. On the other hand, an increase in the ZNO seed layer thickness deposited by the sol-gel spin coating resulted in a worsening of the c-axis alignment. This may be due to surface impurities, as increased deposition by sol-gel spin coating results in the increase in exposure to impurities. Smoother seed layer surfaces result in more aligned nanowires as opposed to rougher surfaces.

The RF cylindrical magnetron sputtering technique resulted in a higher abundance of the mean ZnO nanowire diameter compared to the sol-gel spin coating technique which results in a more diverse ZnO nanowire diameter range.

II Gold Layer Thickness

An increase in the gold (111) film layer thickness decreases the mean diameter of ZnO nanowires and, concurrently, increases the nanowire density. An increase in the Au (111) film layer thickness resulted in a worsening in the c-axis alignment of the ZnO nanowires. The results show that the presence of an Au film layer beneath the ZnO seed layer affects the morphology of the synthesized ZnO nanowires.

III Gold Film Crystal Orientation

Polycrystalline gold resulted in an increase in the mean ZnO nanowire diameter, whereas single crystalline gold (111) resulted in a decrease in the mean diameter ZnO nanowire and a concomitant higher density of ZnO nanowires on the seed layer. The crystal orientation of the gold film layer had no effect on the c-axis alignment of the synthesized ZnO nanowires.

From the results, it can be seen that numerous factors need to be taken into account when synthesizing ZnO nanowires. The optimal ZnO nanowire structure in a transducer is one with the smallest diameter and which is perfectly orientated. The results show the importance of the initial quality of the ZnO seed layer. The seed layer deposition technique, RF magnetron sputtering produces a more uniform ZnO seed layer with seed grains of similar sizes, as opposed to the sol-gel spin coating technique. Metal surfaces beneath the ZnO seed layer effects the growth of ZnO nanowires. The quality of the metal film layer, in turn, effects the quality of the deposited ZnO seed layer and, hence, the quality of the synthesized ZnO nanowires For exemplary purposes an embodiment of the system for the detection of biomolecules and its characterisation is described herein below. The system may be used to detect antibodies (immunoglobulins). An antigen, in this case lysozyme, is immobilized onto gold-coated ZnO nanowires by covalently binding the lysozyme to SAMs on the gold coating. The semiconductormetal interface between the ZnO nanowires and the gold coating (electrode) forms a Schottky barrier so that changes in voltage can be measured. Immobilization of lysozyme onto ZnO nanowires was studied by atomic force microscopy (AFM), Fourier transform infrared (FTIR) spectroscopy and fluorescence microscopy. The characteristics of the system were studied by AFM, scanning electron microscopy (SEM), transmission electron microscopy (TEM) and X-ray diffraction (XRD).

EXAMPLE

The preparation of the embodiment of the system for the detection of biomolecules can be divided into 4 steps:

1. Preparation 1.1 Substrate Preparation

Silicon (100) wafers were cut into 1×1 cm sizes and sonicated for 10 min in acetone, followed by sonication for 10 min in absolute ethanol and 10 min in distilled water. The wafers were dried under nitrogen gas and placed on a hot plate at 110° C. for 5 min. A 20 nm layer of titanium (Ti) was deposited onto the silicon wafers by using RF cylindrical magnetron sputtering (50 to −400 V, 0.5 A, 100 W, 21 kHz, $2\times10^{-2}$ mbar in the presence of 60% argon). The coated wafers were cleaned by immersion in absolute ethanol for 10 s, dried and heated, as described before, and then coated with 40 nm gold. A Quorum sputter coater (Quorum Technologies Ltd, West Sussex, UK), set at 90°, 1.5 kV, 20 mA and operated under $2\times10^{-1}$ mbar argon pressure, was used. The gold-coated substrates were cleaned by immersion in gold cleaning solution (Sigma Aldrich, MO, USA) for 30 s, rinsed with distilled water for 30 s and dried under nitrogen gas.

ZnO seed layers were deposited onto the gold-coated wafers by using the sol gel spin coating technique. In short, this involved the following: 0.75 M zinc acetate dehydrate ($C_4H_{10}O_6Zn$) was dissolved in a mixture of 2-methoxyethanol ($C_3H_8O_2$) and monoethanolamine ($C_2H_7NO$) at 25° C. The molar ratio of monoethanolamine to zinc acetate was 1:1. The solution was stirred for 1 h at 60° C., after which 25 pl was placed onto the gold-plated silicon wafers and spun in a Laurell WS-400-6NPP spin coater (Laurell Technologies, PA, USA) at 6000 rpm for 30 s. After spin-coating, the wafers were dried at 200° C. for 5 min on a hot plate to evaporate the solvents and remove residual organic components from the film layer. The ZnO seed layers were then annealed in air at 700° C. for 10 min.

1.2 Synthesis of the ZnO Nanowires

Zinc oxide nanowires were synthesized using the hydrothermal growth method. Wafers coated with a ZnO seed layer were placed facing down on a solution of 0.01 M zinc nitrate hexahydrate [$Zn(NO_3)_2.6H_2O$] and 0.01 M hexamethylenetetramine ($C_6H_{12}N_4$) in distilled water for 7 h in an oven at 90° C. The coated wafers were then washed with distilled water to remove the residual salts and amino complexes, dried under nitrogen gas and placed on a hot plate at 110° C. for 5 min. The wafers were then baked at 350° C. for 30 min.

1.3 Schottky Barrier Formation

The ZnO nanowire-coated wafers were spun-coated with 50 μl of poly(1-vinylpyrrolidone-co-2-dimethylaminoethyl methacrylate) (PMMA; 3.04%, w/w), using a Laurell WS-400-6NPP spin coater at 7000 rpm for 30 s. The wafers were dried at 120° C. for 5 min and then coated with a 10 nm layer of gold at 70°, using a Quorum sputter coater, set at 1.5 kV and 20 mA and operated at $2\times10^{-1}$ mbar in the presence of argon. The PMMA layer served as an insulator between the two gold layers. The metalsemiconductor junction that formed between the gold film layer and the ZnO nanowires creates a Schottky barrier. To verify the formation of a Schottky contact, respective IV curves were obtained for the nanowires and the constructed biosensor.

1.4 Protein Immobilisation

Glass containers were cleaned with piranha solution [30:70 (v/v) $H_2O_2$ and $H_2SO_4$] to avoid contamination and rinsed three times with absolute ethanol. Alkanethiol, 3-mercaptopropanoic acid (1 mM) was dissolved in absolute ethanol by sonication for 5 min at 25° C., and the pH adjusted to 2.0. The gold-coated ZnO nanowires were immersed in the self-assembled monolayer (SAM) solution for 24 h at 25° C. in a Schlenk reaction vessel filled with nitrogen gas (99.9%). Self-assembled monolayers are organic molecules that self-assemble onto surfaces to form an order domain which can be used as molecular scaffolds onto which proteins can be immobilized. The formation of self-assembled monolayers was terminated by rinsing the nanowires three times with absolute ethanol.

Nanowires bound with self-assembled monolayers were incubated in the presence of chemical linkers to form SAM-intermediates reactive to primary amino groups of proteins. The self-assembled monolayers were exposed to 5 mM EDC (>99%) [ethyl (dimethylaminopropyl) carbodiimide] and 5 mM (>97%) NHS (N-hydroxysuccinimide) in absolute ethanol (pH 7.0), under nitrogen gas atmosphere at 25° C. for 3 h. The combination of EDC and NHS increased the coupling efficacy and created a more stable reactive intermediate.

The biosensors were rinsed with phosphate buffered saline (PBS) (137 mM NaCl, 2.7 mM KCl, 10 mM $Na_2HPO_4.2H_2O$, 2 mM $KH_2PO_4$, pH 7.2) for 10 s, immersed into PBS containing lysozyme (1 mg/ml) from hen egg white (Roche, Mannheim, Germany) and left at 4° C. for 24 h under nitrogen gas atmosphere. Proteins immobilized onto the biosensors were rinsed with PBS for 10 s, dried with nitrogen gas and stored at 4° C. under nitrogen gas atmosphere.

The embodiment of the system for the detection of biomolecules, specifically the ZnO nanowires that was grown by a solvothermal method and the protein immobilisation steps described above were characterised by suitable methods.

2. Characterisation 2.1 Characterisation of ZnO Nanowires

A Nanosurf AFM Easyscan 2 (Nanosurf Inc., CA, USA) was used to characterise the surface topology of the deposited ZnO seed layers and to determine the surface roughness. The morphology, diameter and density of the synthesized ZnO nanowires were evaluated using a FEI Nova NanoSEM 230, equipped with a TLD detector (FEI, OR, USA). The purity and elemental composition of the ZnO nanowires were analysed using a FEI Nova NanoSEM 230, equipped with an X/Max Oxford energy-dispersive X-ray (EDX) detector (Oxford Instruments, UK) that covered a detector area of 20 $mm^2$. EDX spectrums were analysed using INCA software (Inca Software, Berkshire, UK).

Transmission electron microscope (TEM) micrographs and selected area electron diffraction (SAED) patterns were collected with a Philips Tecnai TF20 TEM (FEI, OR, USA), equipped with a field emission gun and operated at an accelerating voltage of 200 kV. High resolution transmission electron microscopy (HRTEM) images were used to analyse the crystal structure of the ZnO nanowires and to determine the direction of axial growth. The mean length and diameter of the synthesized ZnO nanowires were determined from TEM micrographs. ZnO nanowires were scratched from the substrate surface, dissolved in absolute ethanol and sonicated for 10 s. A drop of the liquid was placed on a copper (Cu) grid, of which the back was covered with a carbon film layer. The samples were allowed to air dry before microscopy.

The Au film layer, ZnO nanowire crystal structures and phase compositions were determined by XRD, using a Bruker AXS D8 Advance X-ray diffractometer operated in locked coupled mode (Bruker AXS, Frankfurt, Germany). The instrument was equipped with a Vantec-1 position sensitive detector optimized for Cu-Kα radiation with A=1.5406 Å. The X-ray tube was operated at 40 mA and 40 kV and measurements were recorded at a scanning rate of 0.5 s/step, with a step size of 0.014° in a 29 range extending from 31.28° to 149.3°.

2.2 Characterisation of Protein Immobilisation

The surface topology of the immobilized lysozyme was studied using an atomic force microscope (AFM) and images were collected with a Nanosurf AFM Easyscan 2. Images were acquired in tapping mode at a scan rate of 2 Hz with a platinum (Pt) cantilever (spring constant of 0.06 $Nm^{-1}$), a drive amplitude of 20-50 mV and set-points in the range of 0.14 V.

Infrared (IR) spectra of the monolayers were obtained to confirm self-assembled monolayer (SAM) formation, observe chemical modifications of the SAM functional groups and to detect the immobilization of lysozyme. Attenuated total reflectance-Fourier transform infrared (ATR-FTIR) spectra were recorded in the range of 500-4000 $cm^{-1}$ by using a Thermo Scientific Nicolet iS10 FTIR (Thermo Scientific Inc., MA, USA) spectrometer. ATR-FTIR spectra were collected using 300 scans with a 4 $cm^{-1}$ resolution. Background noise and atmospheric suppression were subtracted by using OMNIC software (Thermo Scientific Inc., MA, USA).

Surface coverage of the immobilized lysozyme was assessed using fluorescence microscopy. Lysozyme functionalized biosensors were incubated with 100~g/ml rabbit primary lysozyme antibody serum (Rockland Immunochemicals Inc., PA, USA) suspended in caseinPBS (1% casein in PBS, pH 7.2) for 30 min at 25° C. and thereafter washed for 5 min in caseinPBS. Protein functionalised nanowires bound with primary antibodies were incubated with 10~g/ml Alexa Fluor 488 goat anti rabbit H+L IgG (Life Technologies, CA, USA) in caseinPBS for 30 min at 25° C. in the dark, followed by washing for 5 min in caseinPBS. Non-specific binding of the secondary antibody conjugate and lysozyme to the biosensor surface was assessed by incubating the biosensor for 1 h in the presence of the secondary antibody and lysozyme, respectively. Confocal images were acquired with a Carl Zeiss Confocal LSM 780 Elyra Si scanning laser microscope, equipped with a SR-SIM super resolution platform (Carl Zeiss, Oberkochen, Germany) and a 100× oil-immersion lens. An argon/krypton laser excited the Alexa Fluor 488 at 488 nm and emitted light detected at 493-630 nm.

2.3 In Vitro Testing of the Embodiment of the System for the Detection of Biomolecules A lysozyme-functionalized system for the detection of corresponding antibodies was fixed to a test-board as shown in FIG. 2. The biosensor was positioned in the centre. The two opposite corners were connected with silver paste to a conducting line, which was in turn connected to the receiver. The anode of the biosensor was connected to ground and the cathode to the positive terminal of the receiver. Binding of antibodies to the gold-coated ZnO nanowire constructs induce bending of the nanowires and/or the application of tensile pressure, which results in a piezoelectric potential. Changes in voltage readings were measured using an operational amplifier with a gain of 100 V/V (Texas Instruments Inc., TX, USA), as shown in FIG. 3. The amplified signal, in analogue format, was converted to a digital signal using a LabJack U6 converter (LabJack Corporation, CO, USA). The digital signal was analysed using DAQFactory software (Azeotech Inc., OR, USA).

Before readings were recorded, the background voltage of the system for the detection of antibodies was measured. The system was exposed to monospecific lysozyme antiserum at concentrations of 10 ng/ml, 50 ng/ml, 500 ng/ml, 1~g/ml, 10~g/ml and 20~g/ml (Rockland Immunochemicals Inc., PA, USA). Antibodies were suspended in PBS, placed on the surface of the system, incubated for 1 h at 25° C., washed with PBS for 30 s, dried with nitrogen gas and then analysed.

3. Results

Figure 6:
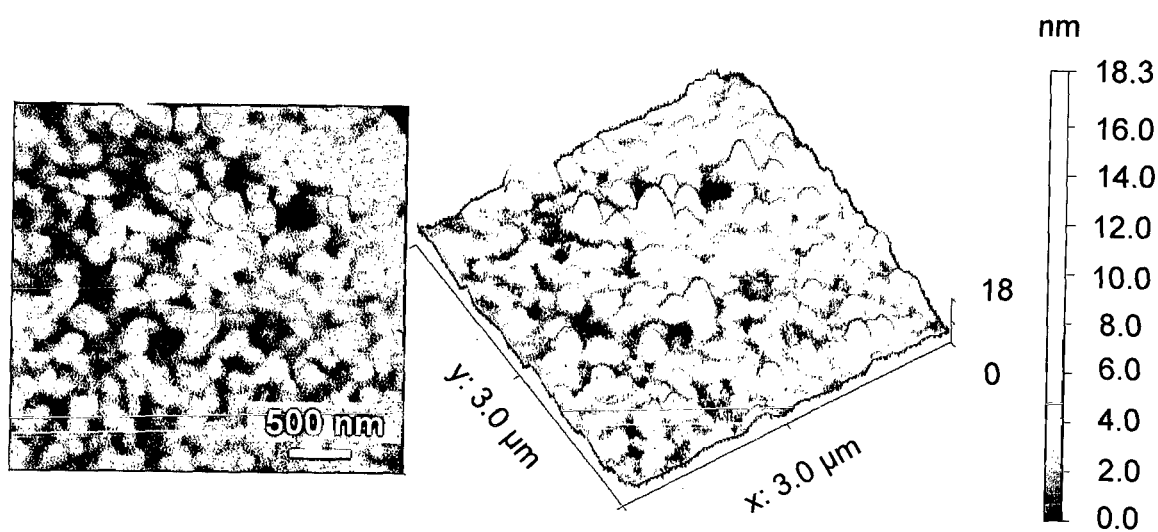
FIG. 6 is a three-dimensional AFM image of the surface topology of a ZnO seed layer deposited by the sol-gel spin coating technique.
Figure 7A:
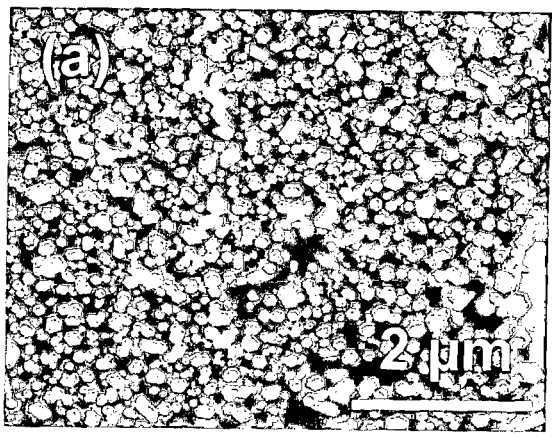
FIG. 7A is a high magnification FEI-SEM image of a top view of the ZnO nanowires grown using the hydrothermal method.
Figure 7B:
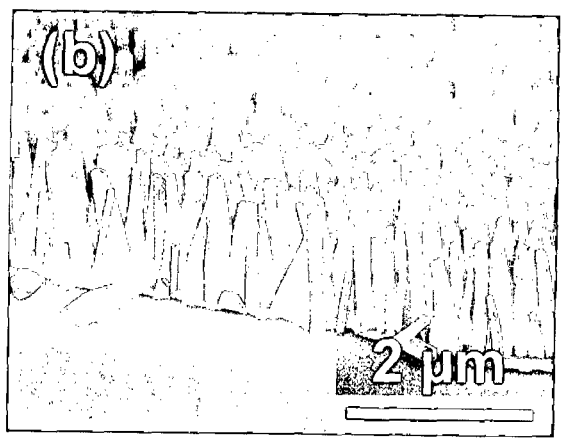
FIG. 7B is a high magnification FEI-SEM images of a 50° tilted view of the ZnO nanowires of FIG. 7 A.
Figure 7C:
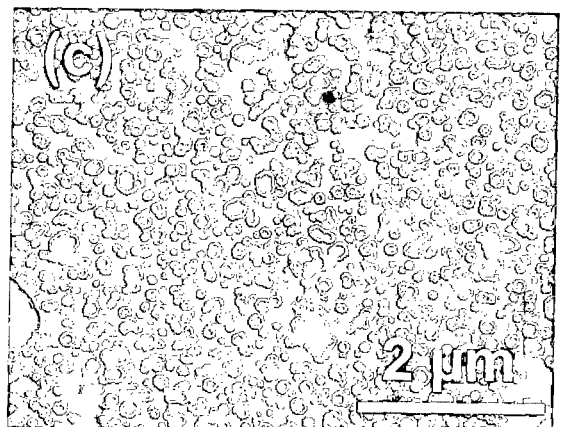
FIG. 7C is a high magnification FEI-SEM images of a top view of ZnO nanowires that have been spin-coated with PMMA and have a 10 nm gold layer deposited thereon.

The ZnO seed layer, shown in FIG. 6, had a mean grain length of 8.5 nm, a mean diameter of 89 nm (σ=22) and a root-mean square surface roughness of 2 nm. The mean diameter of the ZnO nanowires, calculated from the relative diameter abundance of 1000 ZnO nanowires, was 78 nm (σ=35) and they were grouped 108 per $m^2$. FIG. 7A is a high magnification top FEI-SEM image of vertically aligned ZnO nanowires that were grown using the hydrothermal method. The nanowires are uniformly distributed and mainly c-axis oriented, i.e. with their longitudinal axes perpendicular to the ZnO seed layer surface as is evident in the 50° tilted FEI-SEM image of the nanowires shown in FIG. 7B. FIG.

Figure 7D:
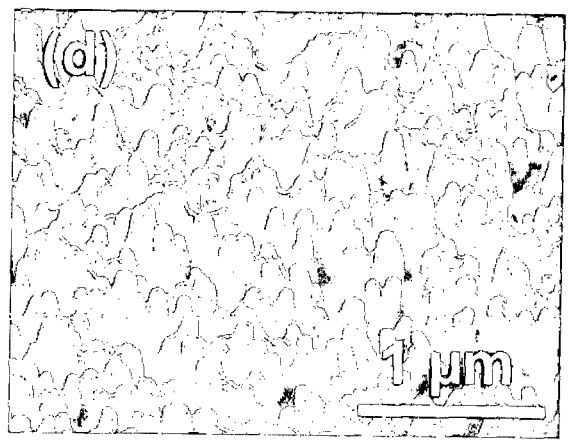
FIG. 7D is a high magnification FEI-SEM images of a 50° tilted view of ZnO nanowires that have been spin-coated with PMMA and have a 10 nm gold layer deposited thereon.

7C is a top FEI-SEM image of the ZnO nanowires after they have been spin-coated with PMMA and a 10 nm layer of gold has been deposited thereon. The ZnO nanowires remained hexagonal after the deposition of PMMA and gold. The filling of the spaces between the ZnO nanowires with PMMA is clearly visible in the 50° tilted FEI-SEM image of the nanowires shown in FIG. 7D. Nanowires protruding from the PMMA layer had an average length of 180 nm ($\sigma$=45).

Figure 8A:
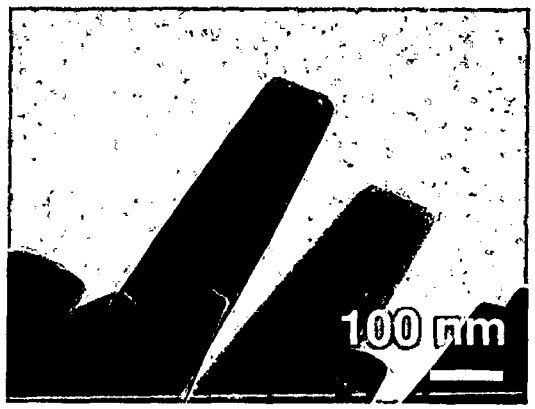
FIG. 8A is a TEM image of ZnO nanowires on a substrate that was used to determine an approximate diameter of a nanowire.
Figure 8B:
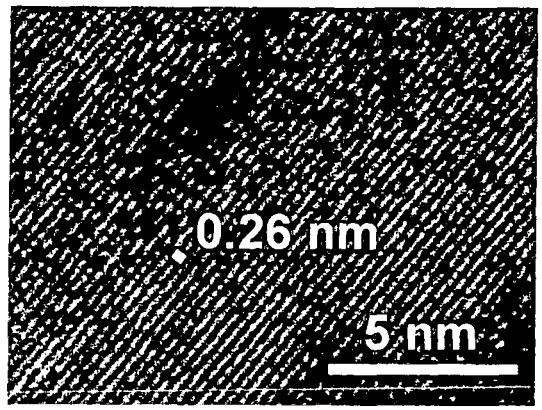
FIG. 8B is an image of the surface of the nanowires recorded with HRTEM, showing a major lattice spacing of 0.26 nm.
Figure 8C:
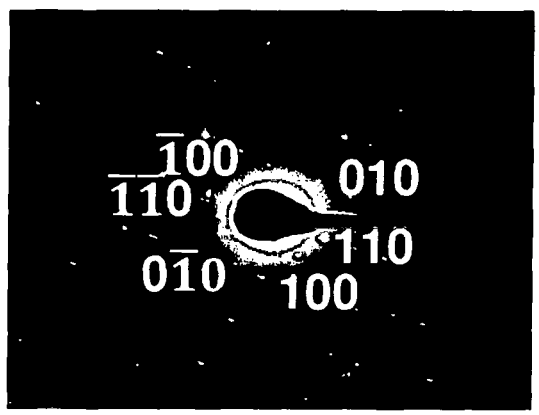
FIG. 8C is a SAED pattern with a single-crystal hexagonal wurtzite structure.
Figure 8D:
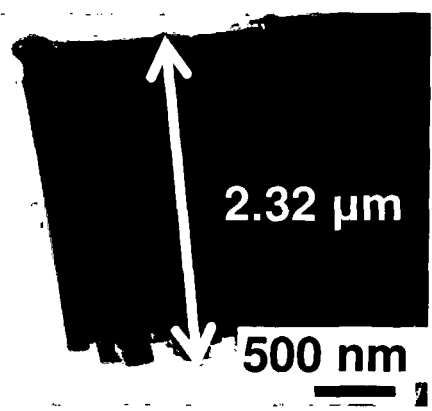
FIG. 8D is a TEM image of ZnO nanowires on a substrate that was used to determine the approximate length of a nanowire.
Figure 8E:
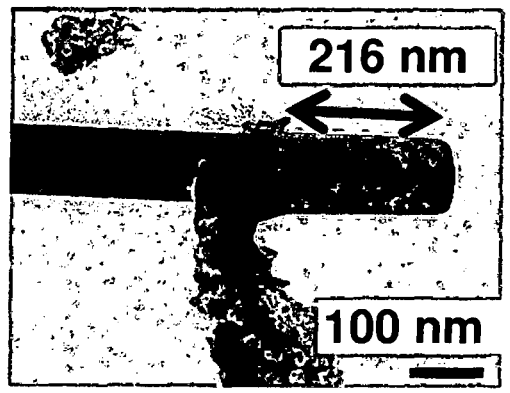
FIG. 8E is a TEM image of a ZnO nanowire showing the average length of ZnO nanowires that protrudes from the PMMA layer.

According to energy dispersive X-ray spectroscopy (EDS), the nanowires were more-or-less stoichiometric (51% Zn and 49% 0). The TEM micrograph image of the ZnO nanowires shown in FIG. 8A reveal that the average nanowire diameter is 93 nm. The average length of the nanowires is 2.3 µm as shown in the TEM image of FIG. 8D. Images recorded with HRTEM showed a major lattice spacing of 0.26 nm as shown in FIG. 8B, which corresponds with the distance of the (002) crystal plane of wurtzite ZnO. According to the SAED pattern, the ZnO nanowires had a single-crystal hexagonal wurtzite structure (FIG. 8C) and grew along the [0001] direction. The average length of ZnO nanowires that protruded from the PMMA layer was 216 nm as shown in FIG. 8E. The coating of the ZnO nanowire protrusions with gold is clearly visible in FIG. 8E.

Based on XRD analysis, the nanowires were mostly orientated perpendicular to the surface (Table 1) and in the direction of the c-axis, with most crystal growth in plane (002) and little growth in crystal planes (100), (101), (102), (103), (004), (202), (104), (203), (105) and (006). The ZnO diffraction peaks that did not overlap with the gold film layer and silicon substrate peaks are shown in Table 1. The XRD pattern of the nanowires, indexed using the JCPDS database, corresponds to hexagonal ZnO.

TABLE 1

XRD pattern of ZnO nanowires grown by the hydrothermal method.

| 2θ | h k l | Intensity (%) |
|---|---|---|
| 31.74 | 1 0 0 | 0.025 |
| 34.43 | 0 0 2* | 100 |
| 36.25 | 1 0 1 | 0.113 |
| 47.54 | 1 0 2 | 0.036 |
| 62.87 | 1 0 3 | 0.113 |
| 72.61 | 0 0 4 | 3.153 |
| 76.95 | 2 0 2 | 0.006 |
| 81.4 | 1 0 4 | 0.046 |
| 89.63 | 2 0 3 | 0.006 |
| 104.17 | 1 0 5 | 0.056 |
| 125.23 | 0 0 6 | 0.007 |

*XRD spectrum is normalised with respect to the (0 0 2) crystal plane.

Figure 9:
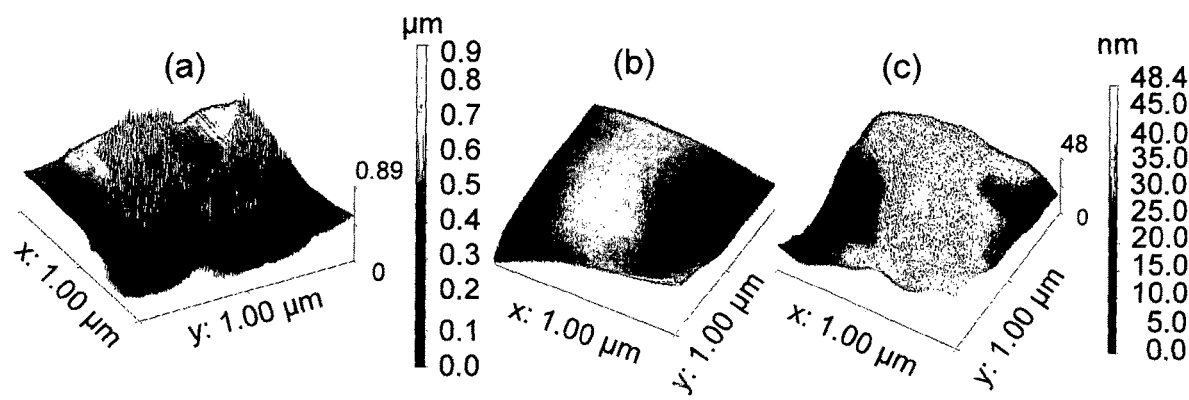
FIG. 9 is a three-dimensional topographic AFM image of (a) the exemplary embodiment of the system for the detection of biomolecules, (b) a smooth surface of the system and (c) a smooth surface of the system immobilised with lysozyme.

Three-dimensional images obtained with AFM showed the topographic images of the embodiment of the system for the detection of biomolecules, a smooth area of the system and a smooth area of the system immobilized with lysozyme (FIG. 9). From these results it is clear that some ZnO nanowires protrude from the PMMA layer, whilst others are totally covered, observed as flat surfaces as shown in (a) of FIG. 9. Lysozyme was immobilized on the surface of the nanowires, as evident from the increase from 0.65 nm to 0.90 nm in the root mean square surface roughness.

Figure 10:
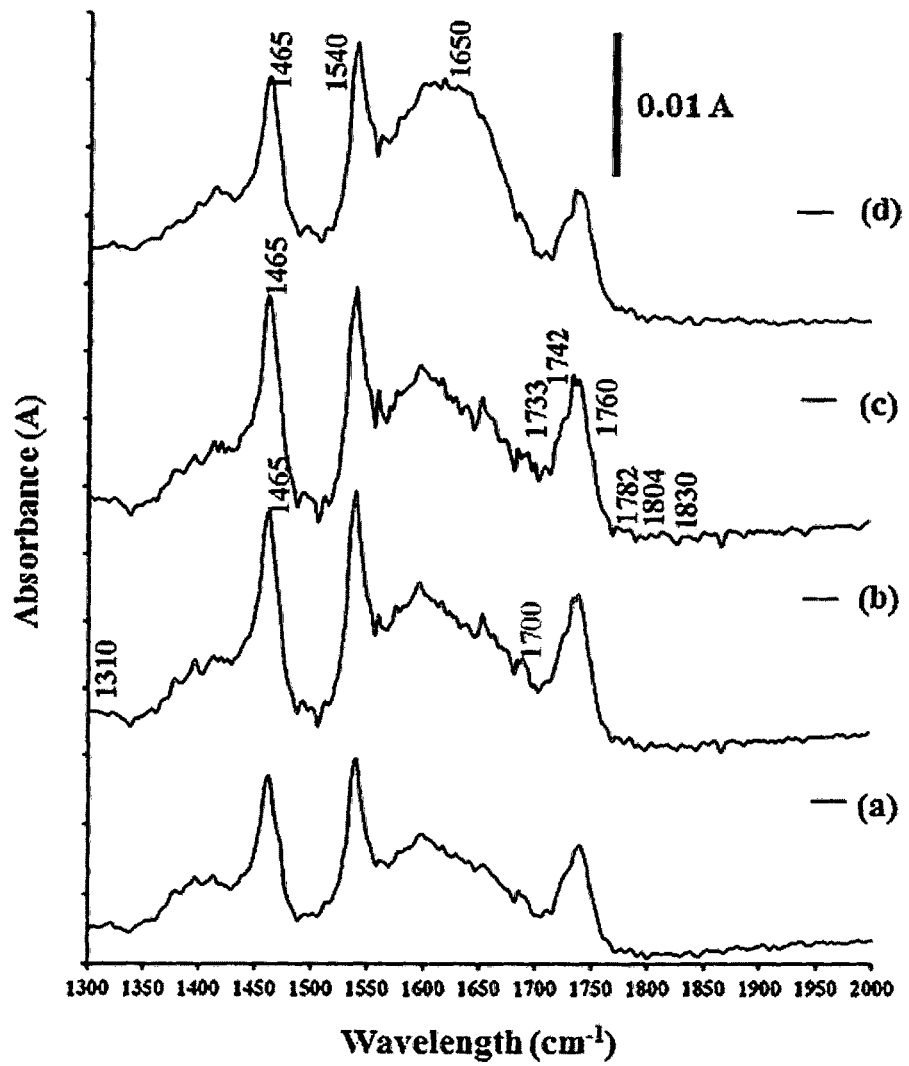
FIG. 10 is a collection of FTIR spectra of (a) the biosensor surface, (b) the surface bound with the 3-mercaptopropionic acid SAM, (c) the SAM modified by EDC/NHS esterification and (d) the surface covalently immobilised with lysozyme.
Figure 11:
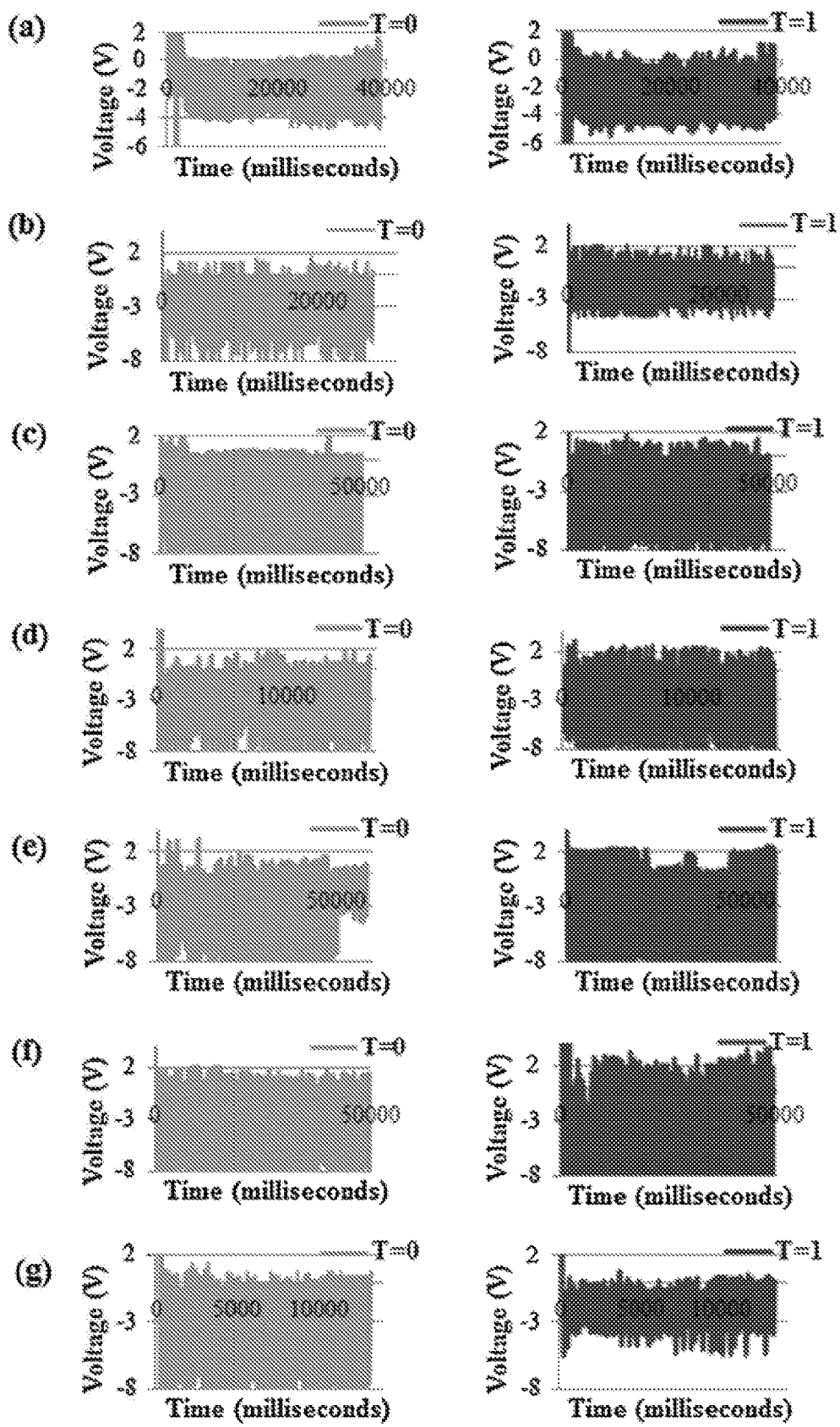
FIG. 11 is the voltage output of the system for the detection of antibodies prior to analysis and after incubation for 1 hour with primary lysozyme antibodies with a concentration of (a) 10 ng/ml, (b) 50 ng/ml, (c) 500 ng/ml, (d) 1~g/ml, (e) 10~g/ml and (f) 20~g/ml and (g) 0 ng/ml (negative control)

ATR-FTIR scans of the surface of the system shown in FIG. 10 reveal changes in surface chemistry that occurred after monolayer formation, the activation of the SAM with EDC/NHS and the immobilization of lysozyme. SAM formation was confirmed by the presence of a strong peak at 1700 cm$^{-1}$ in spectrum (b) of FIG. 10, which corresponded to the v(C=O) free carboxylic acid stretch of carbonyls. Carbonyl stretching frequencies in this range are characteristic of dimerization or other intermolecular hydrogen bonding processes available to the carbonyl terminated SAM. Additional peaks at 1310 cm$^{-1}$ and 1465 cm$^{-1}$ in spectrum (b) of FIG. 10 are characteristic of alkane groups. The peak at 1310 cm$^{-1}$ was assigned to the C—H scissors vibration mode for alkanes and the peak at position 1465 cm$^{-1}$ to CH bending of methylene chains. The presence of these peaks indicated that carboxylic acid terminated SAM 3-mercaptopropanoic acid formed on the gold-coated ZnO nanowire constructs.

The EDC/NHS esterification spectra displayed a different FTIR profile. The peak at 1742 cm$^{-1}$ in spectrum (c) of FIG. 10 corresponded to the v(C=O) asymmetric carbonyl stretch of NHS esters, contributed by the succinimidyl carbonyl group. Two smaller peaks formed at 1830 cm$^{-1}$ (NHS-ester carbonyl stretch) and 1782 cm$^{-1}$ (NHS-ester C=O symmetric stretch) and are attributed to the band splitting of the ester carbonyl C=O stretching vibration. Peaks at 1733 cm$^{-1}$ (ester C=O stretch of N-acylurea), 1760 cm$^{-1}$ (anhydride asymmetric C=O stretch) and 1804 cm$^{-1}$ (anhydride symmetric C=O stretch) are by-products of the EDC/NHS esterification chemistry. The presence of these peaks indicated that EDC/NHS esterification of the carboxylic acid groups occurred. Addition of lysozyme to the chemically activated surface resulted in the presence of characteristic bands at 1540 and 1650 cm$^{-1}$ (spectrum (d) of FIG. 10). The peak at 1650 cm$^{-1}$ can be assigned to amide I (C=O stretch) and 1540 cm$^{-1}$ to amide II (NH bend and CN stretch combined) modes. The presence of these two peaks indicated that lysozyme was covalently immobilized to the SAM and thus subsequently to the gold-coated nanowire constructs.

Fluorescence microscopy was used to assess the surface loading of lysozyme to the biosensor surface. The lysozyme functionalised system was incubated with primary lysozyme antibodies and secondary lysozyme fluorescent antibody conjugates. Lysozyme was immobilized to the nanowire surface. Non-specific binding of the secondary antibody conjugate and lysozyme to the surface was assessed. The relative fluorescence intensity of the immobilized lysozyme on the surface was 287 RFU, non-specific binding of the secondary antibody conjugates was 8 RFU, and non-specific binding of lysozyme was 10 RFU. Based on these results, lysozyme was immobilized to the SAMs, as the fluorescence intensity was not contributed by non-specific binding of the secondary antibody conjugate or lysozyme to the biosensor surface.

The nonlinearity of the IV curve indicated that a Schottky contact formed at the nanowire-electrode interface.

Figure 12A:
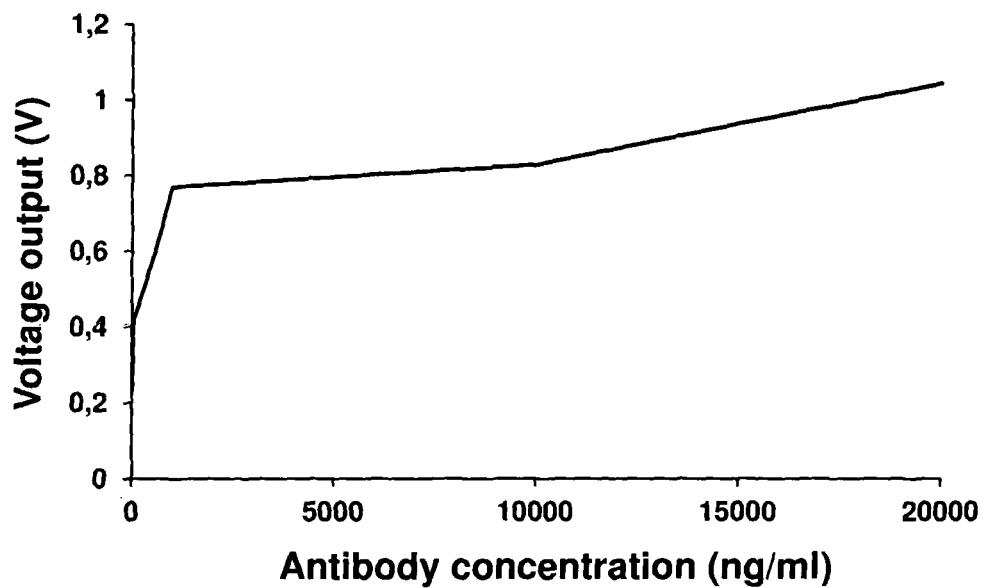
FIG. 12A is a plot of the voltage output as a function of the antibody concentration within a concentration range of 0.05 to 20 µg/ml; and, FIG. 12B is a plot of the c the voltage output as a function of the antibody concentration within a concentration range of 0.01 to 1 µg/ml.
Figure 12B:
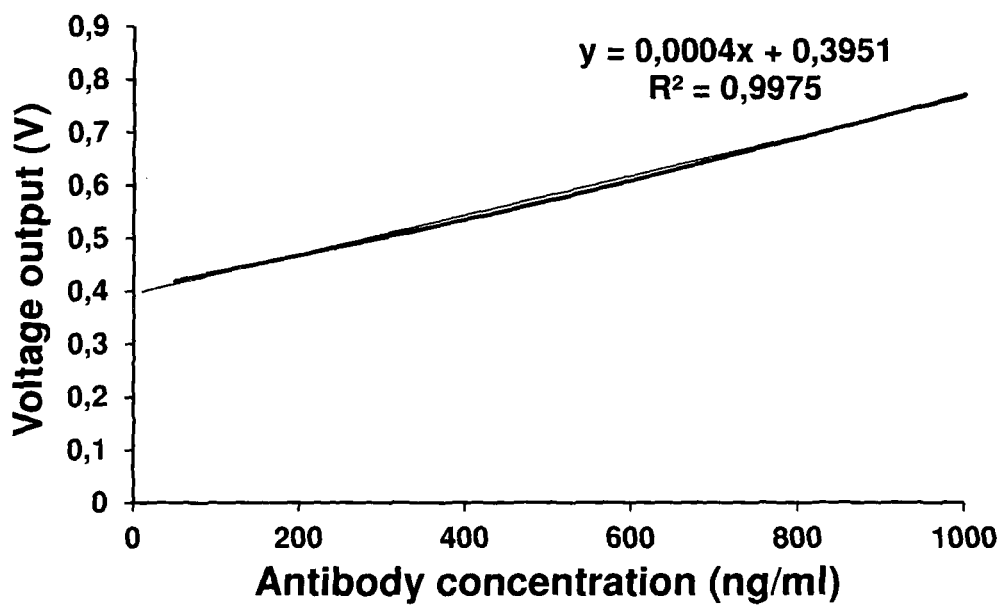

Next in vitro tests were conducted using monospecific antibody serum specific for lysozyme. Different concentrations were placed on the surface of the system for the detection of biomolecules and incubated for 1 h to allow bio recognition. Voltage measured for the system prior to analysis and after incubation with different antibody concentrations is shown in FIG. 12. The background voltage produced by the system was measured to determine the background signal in order to differentiate between noise and a positive signal. Background signals arise from disoriented nanowires or pressure applied by the immobilized antigen. Before the addition of 10 ng/ml antibodies (FIG. 12 (a)) the system produced an average voltage of 0.233 V. This increased to 0.497 V after incubation with antibodies (LI=0.264 V). The average voltage produced from 50 ng/ml antibodies before the addition was 0.928 V (FIG. 12 (b)), but increased to 1.347 V after the incubation with antibodies (LI=0.419 V). The system incubated with 500 ng/ml antibodies (FIG. 12 (c)) produce an average voltage of 1.493 V before the addition and an average voltage of 2.063 V after the incubation (LI=0.570 V). Before the addition of 1~g/ml antibodies, an average voltage of 1.551 V was recorded (FIG. 12 (d)). An average reading of 2.321 V (LI=0.770 V) was recorded after incubation (FIG. 12 (d)). Before the addition of 10~g/ml (FIG. 12 (e)) antibodies, the system produced an average voltage of 1.484 V. The system produced an average voltage of 2.312 V after incubation with antibodies (LI=0.828 V). Before the addition of 20~g/ml (FIG. 12 (f)) antibodies the system produced an average voltage of 1.838 V and after incubation an average voltage of 2.882 V (LI=1.044 V). The system acting as the negative control (FIG. 12 (g)) in which only PBS-solution was added produced an average voltage of 0.713 V prior to analysis and an average voltage of 0.517 V after incubation (LI=−0.196 V).

To verify that the voltage observed was not mechanical noise due to friction, the ZnO nanowires were covered with a layer of silver. Under these conditions the Schottky contact did not form and no output voltage was recorded. The sensitivity of the system was tested with antibody levels ranging from 10 ng/ml to 20~g/ml. Output voltage increased linearly with an increase in antibody levels from 50 ng/ml to 1~g/ml, followed by a non-linear increase in voltage as antibody levels were raised to 20~g/ml (FIG. 13A). This indicated that the biosensor was saturated after binding to an antibody concentration of 1~g/ml. A linear response of the piezoelectric biosensor was recorded with antibody concentrations ranging from 50 ng/ml to 1~g/ml (FIG. 13B). The limit of detection (LOD; the signal to noise ratio 3:1) was calculated as 102.76 ng/ml, using the linear equation in FIG. 13B.

Reproducibility was tested by using three biosensors incubated with 1~g/ml lysozyme antibodies. The average readings recorded were 0.722, 0.770 and 0.691 V, respectively. The standard deviation recorded amongst the three biosensors was 3.98%. Stability of the biosensor decreased over time, with 78% activity retained after two weeks of storage under nitrogen gas atmosphere at 4° C. The self-assembled monolayer (SAM), which is used as an attachment monolayer for the immobilization of lysozyme to the ZnO nanowire construct, oxidizes over time. This leads to protein leaching and a decrease in the sensitivity of the biosensor. The sulphur moiety of alkanethiol SAMs are oxidized in the presence of oxygen, ozone and UV light, leading to the detachment of the molecule from the surface.

The above described example of a system for the detection of biomolecules in which an antigen, specifically lysozyme, is immobilised on the surface of the system was included for exemplary purposes only. It will be appreciated by those skilled in the art that various embodiments of the system incorporating different components and/or materials with the same or similar properties as those described exist without departing from the scope of the invention. For instance, gold coatings are used as electrodes, however any material with the same or similar conductivity as gold may be used. Similarly the silicon substrate may be made of another material as long as it performs the same function.

It will be apparent to those skilled in the art that any type of biomolecule for which a complementary biomolecule, capable of interacting and associating with the biomolecule, can be immobilised to the surface of the system by any appropriate connection means. The biomolecule can be any relatively large molecule such as a protein, polysaccharide, glycoprotein or glycolipid. Subject to the identity of the biomolecule, any appropriate molecular scaffold or SAM capable of forming a covalent bond with the biomolecule may be provided on the surface of the system.

Depending on the application of the system, either an antigen or an antibody may be immobilised on the surface of the system. For instance, an antigen or immunogen may be bound to the surface if the purpose of the device is to detect complementary antibodies to the antigen. The fairly immediate presence of the antibodies is indicative of an immune response that has occurred prior to the introduction of the detection system into the biological fluid of a patient and is useful information for the diagnosis of an infection. In an alternative embodiment of the system, an antibody is immobilised on the surface of the system to detect antigens in biological samples or water to directly detect an infection or contamination.

The system for the detection of biomolecules may be used for in vitro detection of biomolecules in samples, or the system may be encapsulated such that it can be swallowed by a patient for in vivo detection of biomolecules. In the case of in vitro detection methods, a wide variety of different sample types may be tested, i.e. biological samples such as body fluids, or water samples. In the case of in vivo detection methods, it will be apparent to those skilled in the art that suitable connection means between the part of the system that is in the body of the patient and the part of the system that remains external to the body, i.e. the operating system, will be provided.

It will further be appreciated by a skilled person that more than one system for the detection of biomolecules may be combined in a kit. Each system in the kit is selective for a different biomolecule and in conjunction it may be used to concurrently detect the presence of a variety of biomolecules in a sample. In such a case, the piezoelectric signals derived from the different systems must, of course, be distinguishable.

The invention claimed is:

1. A system for detection of biomolecules, comprising a plurality of piezoelectric nanowires having ends mounted on a semi conductive substrate and opposite free ends extending generally parallel in a direction substantially perpendicular to the semi conductive substrate, wherein base portions of the nanowires near the ends mounted on the semi conductive substrate are coated with an insulating layer of material which fills the spaces between the nanowires whilst the free ends remain substantially uncoated by the insulating layer, wherein the free ends of the nanowires are coated with a conductive material layer, and the conductive material layer has biomolecules immobilized onto it, and wherein displacement of the nanowires owing to the association of a second type of biomolecule with the biomolecules immobilized on the conductive material layer at the free ends produces a piezoelectric signal.

2. The system of claim 1, wherein the semi conductive substrate comprises silicon wafers wherein, a first section of a surface of the silicon wafers is coated or partially coated with a layer of titanium or titanium oxide, the titanium/titanium oxide-coated silicon wafers are coated with a conductive layer, and wherein the piezoelectric nanowires are zinc oxide (ZnO) nanowires and a ZnO seed layer is provided on the conductive layer, a second section of the surface of the substrate is coated or partially coated with a conductive layer only, and the first section of the surface acts as a cathode and the second section of the surface acts as an anode.

3. The system of claim 2, wherein the titanium/titanium oxide-coated silicon wafers of the first section are coated with gold.

4. The system of claim 2, wherein the second section of the surface of the substrate is coated or partially coated with gold.

5. The system of claim 1, wherein the insulating layer of material is poly(1-vinylpyrrolidone-co-2-dimethylaminoethyl methacrylate).

6. The system of claim 1, further including:
a board on which the system is mounted; and
a measuring system, the board being in electronic communication with the measuring system and wherein the measuring system comprises a receiver and an amplifier circuit including an operational amplifier that is configured to amplify a voltage obtained from the piezoelectric signal.

7. The system of claim 6, further including:
a converter to which the measuring system is connected, the converter being configured to convert the amplified voltage into a digital signal; and
an operating system with a program that issues machine-readable instructions to record, analyse analyze and process the digital signal for display on an electronic device.

8. The system of claim 1, wherein a part of the system involved with the detection of biomolecules is contained in a capsule.

9. The system of claim 8, wherein the capsule is a gelatin capsule to be swallowed by a patient.

10. The system of claim 1, for detection of viral and/or microbial infection of a biological sample.

11. The system of claim 10, wherein the biological sample comprises body fluids obtained from a patient.

12. The system of claim 1, for the detection of biomolecules from a water sample.

13. The system of claim 1, wherein the conductive material layer is a gold coating.

14. The system of claim 13, wherein the biomolecules are antibodies and/or antigens, and primary amino groups of the antibodies and/or antigens covalently bind to the molecular scaffolds.

15. The system of claim 1, wherein conductive material layer is provided with molecular scaffolds, and the biomolecules are covalently immobilized to the molecular scaffolds.

16. The system of claim 15, wherein the molecular scaffolds comprise self-assembled monolayers (SAMs) of 3-mercaptopropanoic acid.

17. A method of detecting biomolecules, the method comprising the steps of:
immersing a system for detecting biomolecules as claimed in claim 1, within a biological fluid;
measuring a change of voltage with a measuring system; and
determining an amount of biomolecules that is associated with biomolecules immobilised on the system based on the change of voltage.

18. The method of claim 17, wherein the method includes the steps of amplifying the change of voltage measured by the measuring system to produce an amplified voltage signal, converting the amplified voltage signal to a digital signal, recording, analysing and processing the digital signal, displaying the amount of biomolecules detected, and assigning a level of pathogenic infection or contamination.

19. The method of claim 17, wherein the method is carried out in vivo as a method of diagnosing a disease of a patient, and wherein the method includes a step of swallowing a part of the system for detecting biomolecules contained in a capsule or implanting a part of the system for detecting biomolecules.

20. The method of claim 19, wherein the disease is an infectious disease caused by a pathogen.

21. The method of as claimed in claim 17, wherein the method is carried out in vitro for diagnosing disease, and includes the steps of collecting a biological sample from a human, and immersing the system for detecting biomolecules or a part of the system in the biological sample.

22. The method of claim 21, wherein the disease is an infectious disease caused by a pathogen and the biological sample is a body fluid.

23. The method of claim 17, wherein the method of detecting biomolecules includes the step of providing an incubation time so as to allow biomolecules in the biological sample to associate with the biomolecules immobilised by the system.

* * * * *

UNITED STATES PATENT AND TRADEMARK OFFICE
CERTIFICATE OF CORRECTION

PATENT NO. : 10,663,463 B2
APPLICATION NO. : 15/124743
DATED : May 26, 2020
INVENTOR(S) : Leon Milner Theodore Dicks et al.

It is certified that error appears in the above-identified patent and that said Letters Patent is hereby corrected as shown below:

On the Title Page

Item (72), please delete "Deon Nevwling" and insert therefore --Deon Neveling--.

Item (56), under Other Publications, please delete "Deon RP. Nevelinga, Thomas S. van den Heeverb, Willie J. Peroldb, Leon M.T. Dicksa" and insert therefore --Deon RP. Neveling, Thomas S. van den Heever, Willie J. Perold, Leon M.T. Dicks--.

Item (56), under Other Publications, please delete "andquantification" and insert therefore --and quantification--.

Page 2, Column 2, item (56), under Other Publications, please delete "Deon RP. Nevelinga;Thesis entitled "Nevelinga" and insert therefore --Deon RP. Neveling; Thesis entitled "Neveling--.

Signed and Sealed this
Twenty-ninth Day of September, 2020

Andrei Iancu
*Director of the United States Patent and Trademark Office*